United States Patent [19]
Scott

[11] Patent Number: 5,673,706
[45] Date of Patent: Oct. 7, 1997

[54] DIAGNOSTIC DEVICE WITH DETACHABLE WHEEL

[76] Inventor: Jeffrey M. Scott, 111 Westwood Cir., East Hills, N.Y. 11577

[21] Appl. No.: 380,039
[22] Filed: Jan. 30, 1995
[51] Int. Cl.$^6$ ............................................. A61B 19/00
[52] U.S. Cl. .................................................... 128/744
[58] Field of Search ................................. 128/740, 744, 128/774

[56] References Cited

U.S. PATENT DOCUMENTS

| | | | |
|---|---|---|---|
| D. 296,470 | 6/1988 | Leopoldi | D24/23 |
| 3,344,781 | 10/1967 | Allen | 128/744 |
| 5,222,504 | 6/1993 | Solomon | 128/744 |
| 5,316,012 | 5/1994 | Siegal | 128/744 |
| 5,433,211 | 7/1995 | Greenfield | 128/744 |
| 5,474,084 | 12/1995 | Cunniff | 128/744 |

*Primary Examiner*—Max Hindenburg
*Attorney, Agent, or Firm*—Graham & James LLP

[57] ABSTRACT

A diagnostic apparatus for testing nerve pathways through skin sensitivity, including a handle, a support assembly mounted to the handle, an axle affixed to the support assembly, a removable wheel having an axle hole adapted to receive the axle, the wheel having a plurality of tines extending radially therefrom, the tines extending to form a point, and a retaining assembly for securing the wheel on the axle, the retaining assembly being movable relative to the axle to facilitate removal and replacement of the wheel; and a dispenser for dispensing the disposable wheels to facilitate easy replacement and prevent contamination of new wheels from handling.

26 Claims, 3 Drawing Sheets

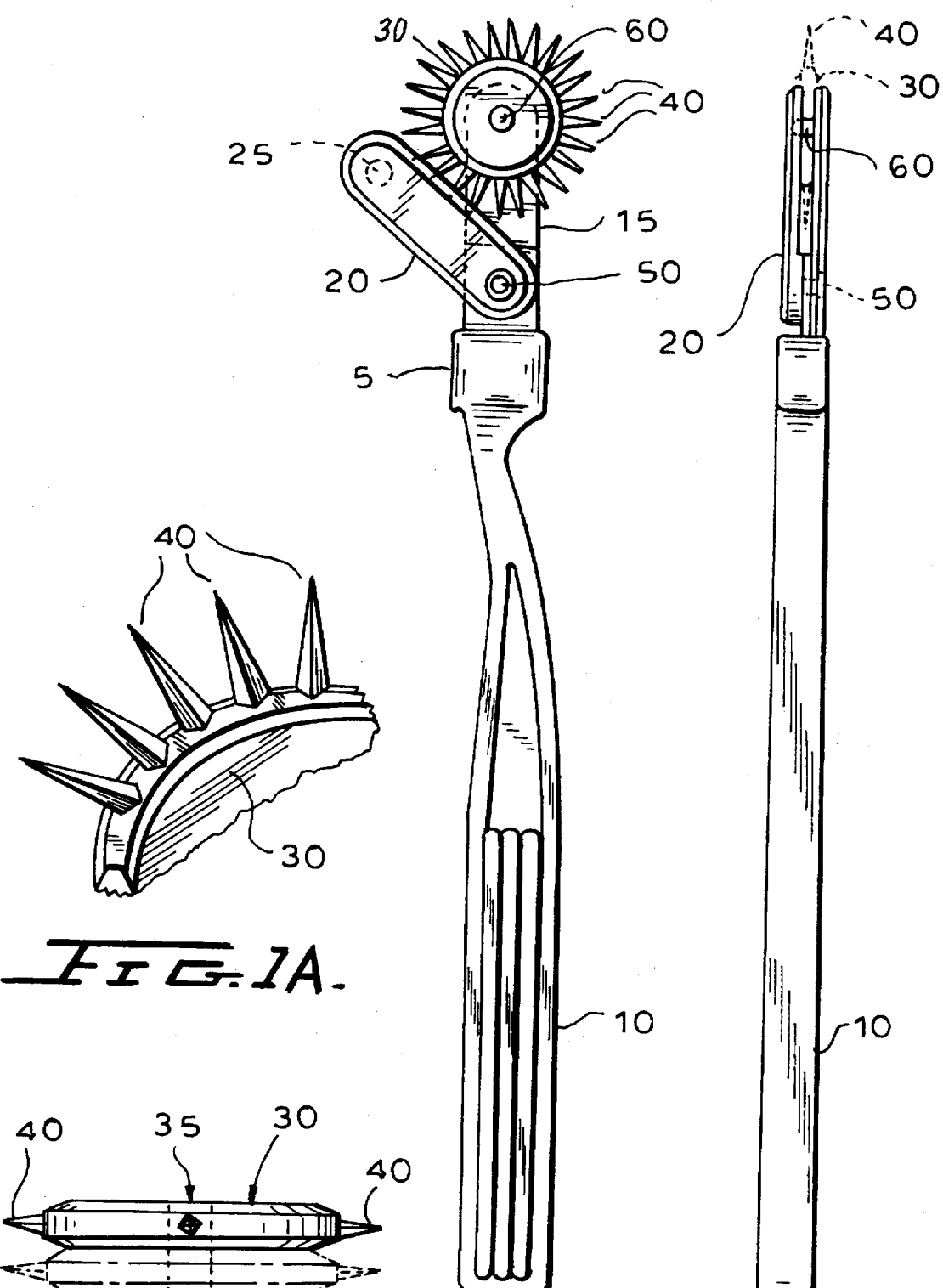
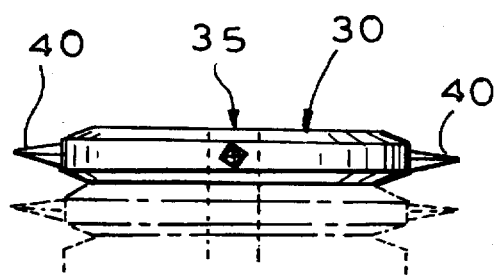

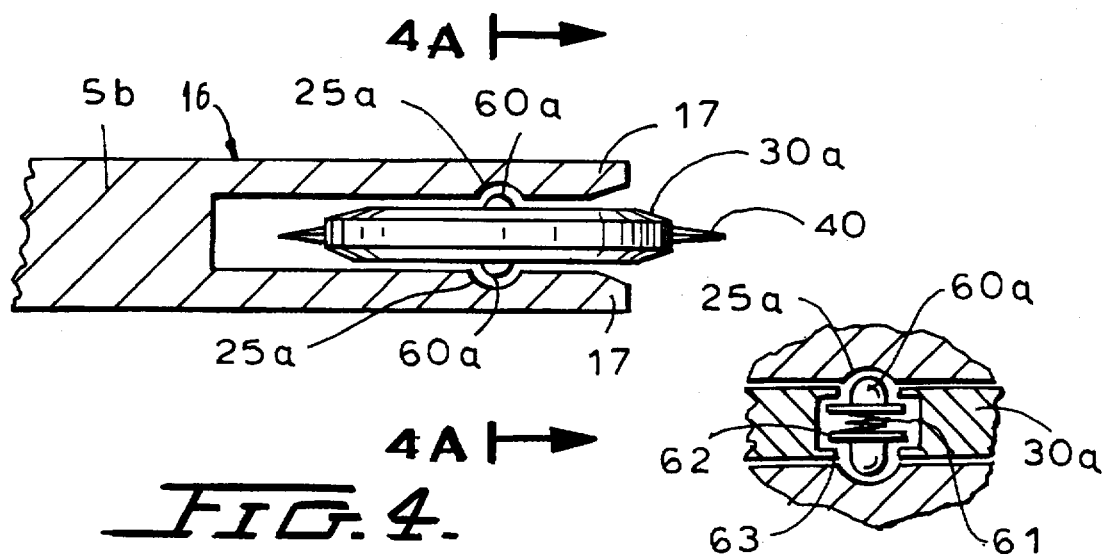
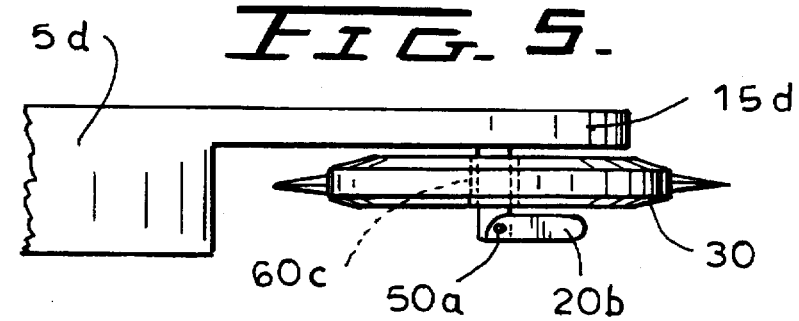
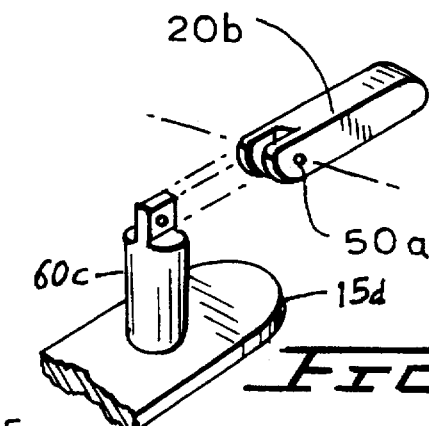
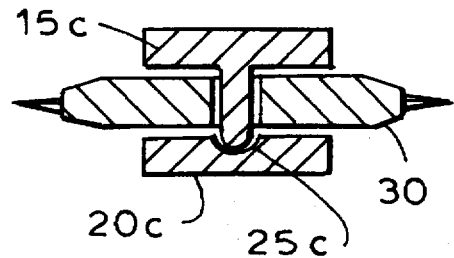
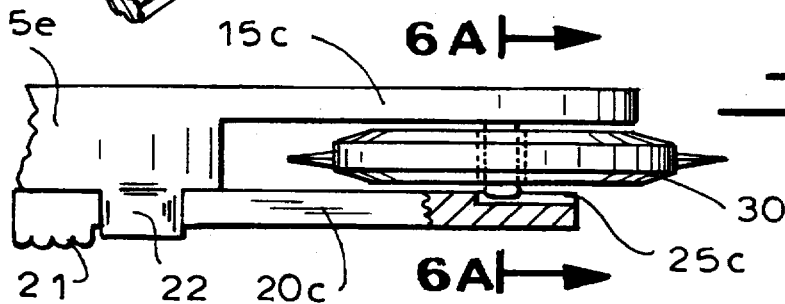

5,673,706

DIAGNOSTIC DEVICE WITH DETACHABLE WHEEL

BACKGROUND OF THE INVENTION

The present invention relates to an improved diagnostic medical device, and in particular to an improvement to the traditional Wartenberg wheel or pinwheel for testing nerve pathways through skin sensitivity. The improvement comprises a retaining apparatus that permits a disposable wheel to be easily removed from and replaced on the handle of the device.

The traditional pinwheel, formed of metal, uses a screw as the axle for attachment of the wheel in place between a pair of fixed forks. A significant drawback of this implementation is that a tool is required for wheel removal and replacement.

For durability and bio-compatibility, the traditional pinwheel is normally made of stainless steel or a comparable metal. This had been thought of as desirable so that the pinwheel device could be sterilized. The inventor has discovered that this is a substantial drawback, because of the possibility of improper sterilization causing the spread of disease. Furthermore, there are substantial costs associated with the labor and equipment required to effect sterilization.

The following patents relating to skin stimulation devices and other similar devices are known to applicant:

U.S. Pat. No. 2,009,526
U.S. Pat. No. 3,590,821
U.S. Pat. No. 3,625,202
U.S. pat. No. 4,823,806
U.S. Pat. No. 5,005,561
U.S. Pat. No. 5,222,504
IT 705824
SU 1641346

None of these devices, however, provides a skin stimulating device with replaceable wheels that inexpensively and effectively prevents the spread of disease.

SUMMARY OF THE INVENTION

It is an object of the present invention to provide a diagnostic tool for testing nerve pathways through skin sensitivity having a disposable wheel made from a light material which provides for a well balanced diagnostic device that is comfortable to hold, easy to handle, and effectively prevents the spread of disease.

The above and other objects of the invention may be achieved by a disgnostic tool comprising a support assembly, an axle affixed to the support assembly, a wheel with an axle hole, the wheel having a plurality of tines extending radially therefrom, and a retaining assembly, to facilitate removal and replacement of the wheel, the retaining assembly being movable in relation to the axle, and adapted to rotatably secure the wheel in position on the axle.

One aspect of the invention may be achieved by an apparatus for testing nerve pathways comprising a wheel having a plurality of tines extending radially therefrom, each of the tines forming a point at a distal end, the wheel also having an axle nub protruding laterally therefrom, a support assembly having an integral handle, the support assembly comprising an axle detent; and a retaining assembly for rotatably securing the wheel in a position with the axle nub of the wheel aligned with the axle detent of the support assembly.

Another aspect of the invention may be achieved by a dispenser for dispensing a wheel having tines, the wheel being for use in testing nerve pathways through skin sensitivity, the dispenser comprising a base portion which provides support for the wheel and is shaped to expose an axle hole of the wheel it supports, a side portion providing a surface from which the dispenser may be handled without contact with the tines of the wheels, a top portion disposed substantially parallel to the base portion, and a spring biasing the wheel away from the top portion and urging the wheel toward the base portion.

Yet another aspect of the invention may be achieved by a dispensing system, comprising a dispenser as described above, a support assembly with an axle affixed thereto, the axle adapted for insertion into the axle hole of the wheel, wherein the dispensing system is adapted for removal of the wheel from the dispenser by inserting the axle into the axle hole and applying a force upon the support assembly in a direction away from the dispenser.

Other features and advantages of the present invention will become apparent from the following description of embodiments of the invention, which refers to the accompanying drawings.

BRIEF DESCRIPTION OF THE DRAWING(S)

Embodiments of the invention will now be described in greater detail in the following detailed description with reference to the drawings in which:

FIG. 1 shows a front view of a first embodiment of the invention showing a diagnostic device in the open position;

FIG. 1A shows a more detailed perspective view of a portion of the wheel of the device shown in FIG. 1;

FIG. 1B shows a side view of a wheel of the device of FIG. 1;

FIG. 2 shows a side view of the device of FIG. 1 in the closed position;

FIG. 4 is a partial cross-section view of a second embodiment of the invention showing the distal end of a diagnostic device;

FIG. 4A is a sectional view of an alternate second embodiment of the invention taken along line A—A of the device in FIG. 4;

FIG. 5 is a partial side view of a third embodiment of the invention showing the distal end of a diagnostic device;

FIG. 5A is an exploded perspective view of the axle and retaining assembly of the device in FIG. 5;

FIG. 6 is a partial side view of a fourth embodiment of the invention showing the distal end of a diagnostic device;

FIG. 6A is a sectional view taken along line B—B of the device in FIG. 6;

DETAILED DESCRIPTION OF EMBODIMENTS OF THE INVENTION

Figure 3:
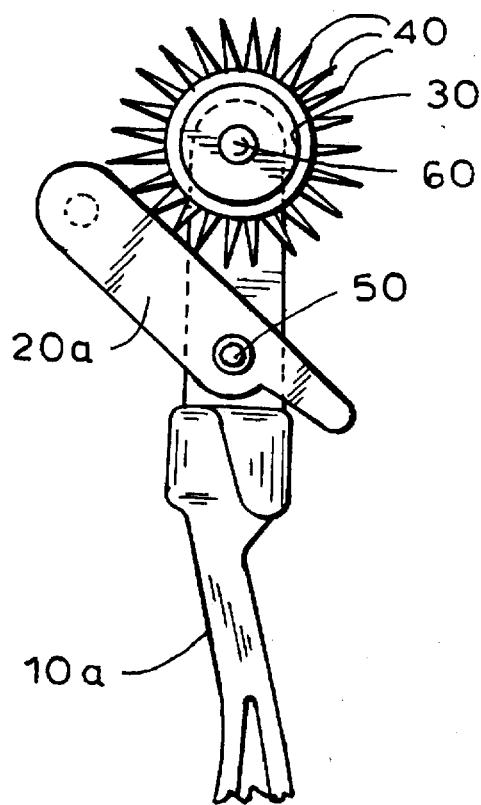
FIG. 3 is partial front view of a variation of the first embodiment of the invention showing a diagnostic device in the open position.

The diagnostic device according to the present invention is used to test nerve pathways to pain sensors through skin sensitivity. Since there are both touch and pain sensors present in the human body, it is often difficult to determine which, if any, of the two sensors are not properly reacting to a particular stimulus. When relatively sharp tines are pressed against the surface of the skin, the pain receptors will react much more heartily than the touch receptors. Thus, for the area where nerve damage is suspected, the diagnostic device according to the present invention can be used to diagnose whether particular areas of the skin are able to sense pain.

First Embodiment

With reference now to the drawings, in FIG. 1 the diagnostic device, generally designated 5, is shown in the open position. The diagnostic device 5 comprises a support assembly 15 with an integral handle 10 at the proximal end thereof. The handle 10 is suitably contoured to be easily manipulated by the hand. A pivot 50 and an axle 60 are connected to the support assembly 15. The pivot 50 pivotally connects the support assembly to a retaining arm 20 which has an axle detent 25.

A wheel 30 having an axle hole 35 and a plurality of tines 40 is adapted to fit on the axle 60. To retain the wheel 30 on the axle 60, the retaining arm 20 can be pivoted around the pivot 50 so as to align the axle detent 25 with the distal end of the axle 60. As shown (in the open position), however, the wheel 30 can be removed from the axle 60 by tilting the device 5 so that the wheel 30 falls off. To prevent the spread of disease, it is desirable to remove the wheel 30 without making contact with the distal ends of the tines 40.

The device 5, including the wheel 30, is made of ABS, an inexpensive, sturdy and durable plastic. Only the wheel 30 is disposable, and thus, it is preferably made from an inexpensive material such as ABS. In the preferred embodiments, however, the device 5 may also be fabricated from ABS due to its excellent properties.

The ridges and contours of the handle 10 are designed for comfort and grip.

Turning to FIG. 1A, it can be seen that the tines 40 are generally pyramidic in shape. The inventor has discovered that the tines 40 are more stable and less susceptible to breakage when formed in a pyramid, as shown, instead of a more traditional conic shape. Further, since the tines 40 and the wheel 30 are made of a plastic, particularly ABS, it was found to be easier and more cost effective to fabricate the tines 40 in a pyramidic shape. (As shown in FIG. 3, however, the tines 40 can also be formed in the traditional conic shape.)

The number of tines 40 and their spacing about the wheel 30 is of interest important. Since cutaneous sensation differs throughout the body (e.g., because the density of sensitivity nerves differs), it is desirable to have the distal ends of the tines 40 spaced sufficiently so that the touch sensors (as opposed to pain sensors) are not substantially aroused where the device is intended to be used. As will be understood by one of skill in the art, the particular spacing of the tines 40 is relevant to the two point discrimination in the areas of the body where the device is used. Essentially, the spacing in this embodiment is far enough apart to avoid substantial stimulation of the touch sensors, but close enough together to provide substantial coverage of the pain sensitivity nerves in areas tested.

Turning now to FIG. 1B, the wheel 30 can be made in any useful diameter. The selection of a diameter is dependent upon the desired: (i) length of the tines 40; (ii) overall dimensions of the device 5; and (iii) overall weight distribution of the device 5. The inventor has found that shorter tines 40 are less succeptable to breakage.

The axle hole 35 is placed in the center of the wheel 30 to permit the wheel 30 to rotate freely about an axle 60. The wheel 30 itself is contoured so that the thickness (i.e., lateral dimension) at the outer perimeter (where the tines 40 are connected) is thinner that the thickness at the center. This has been found to improve the feel of the device 5, and to enable the wheel 30 to spin more freely.

FIG. 3 is a variation of the first embodiment of the diagnostic device 5a according to the invention. The device 5a primarily differs from the device 5 (FIG. 1) in that the retaining arm 20a is shaped to permit the user to rotate the retaining arm 20a into the closed position using a lever. The lever is formed from the proximal end of the retaining arm 20a, which extends substantially past the pivot 50. The pivot 50 thus acts as a fulcrum. As shown in FIG. 3, the support assembly 15a is adapted to conform to the lever portion of the retaining arm 20a when the retaining arm 20a is in the closed position (not shown).

Second Embodiment

Turning to FIGS. 4, a second embodiment of the invention is shown. The device 5b has a support assembly 16 comprising two forks 17 attached to its distal end. Each fork 17 has an axle detent 25a. Fixed axle nubs 60a protrude laterally from each side of wheel 30a.

The axle nubs 60a are rounded on their outer portions to conform generally to the shape of the axle detents 25a. The disposable wheel is inserted using the natural flexibility of the forks 17 which permits the axle nubs 60a to slide across the interior surface of the forks 17 until the axle detents 25a are properly aligned. The interior surface of each forks 17 may be disposed such that it is thinner at its outer edges, thereby permitting easier insertion of the axle nubs 60a into the axle detents 25a.

FIG. 4A shows a variation on the second embodiment wherein a spring 61 which biases the axle nubs 60a away from each other is disposed between the nubs 60a. The nubs 60a are shaped to permit the wheel lip 63 to prevent the nubs 60a from protruding too far, e.g., falling out of the wheel. The rounded shape of the axle nubs 60a also permits the forks 16 to compress the nubs 60a when the wheel 30a is inserted therebetween.

It can be seen that the wheel 30a is inserted into the forks 17 mainly by the compression of the axle nubs 60a; although, depending on the force exerted by the spring 61 and the thickness of the forks 17, some flexing of the forks 17 can also occur during insertion. Once the nubs 60a are aligned with the detents 25a, the spring 61 urges the nubs 60a outward, holding the wheel 30a in place relative to the forks 17.

Third Embodiment

Turning now to FIGS. 5 and 5A, a third embodiment of the invention is shown. The device 5d has a support assembly 15d with an axle 60c affixed thereto. A retaining arm 20b pivotally attached to the support assembly 15d by a pivot 50a. The retaining arm 20b can be pivoted from its closed position (shown) which is perpendicular to the axle 60c, to an open position (not shown) substantially parallel to, and in line with, the axle 60c. When the retaining arm 20b is in the closed position the wheel 30 is retained on the axle 60c, and may spin freely. When the retaining arm 20b is in the open position, the wheel 30 may be easily removed and replaced; for example, by tilting the device 5d and permitting the wheel 30 to fall off.

Fourth Embodiment

FIGS. 6 and 6A show a fourth embodiment of the invention, showing a diagnostic device 5e. In the fourth embodiment, the retaining arm 20c is attached to the support assembly 15c by slide retainer 22. The slide retainer 22 slidably affixes the retaining arm 20c to the support assembly 15c. Placing the device in the open position for removal of wheel 30 from axle 60 is achieved by sliding the retaining arm 20c toward the proximal end of the device 5e. The grip 21 is affixed to the retaining arm 20c. The grip 21 is provided to permit the sliding of the retaining arm 20c, which may be performed with the thumb. The grip 21 may be used to place the device 5e in its open or closed position by sliding the retaining arm 20c. The axle detent 25c may be elongated, as shown, to permit the retaining arm 20c to slide easily toward or away from the axle 60.

Dispenser

Figure 7:
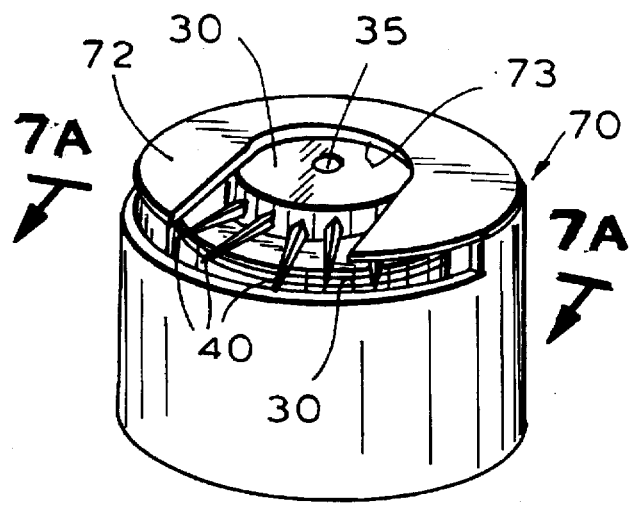
FIG. 7 is a perspective view of one embodiment of a dispensing device for dispensing wheels that are used in conjunction with the device in FIG. 1.
Figure 7A:
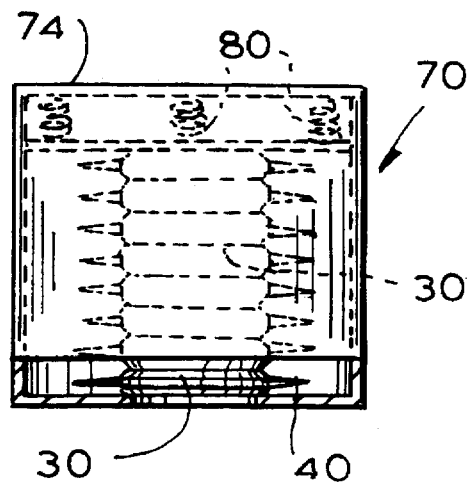
FIG. 7A is a sectional view taken along line C—C of the dispenser in FIG. 7.
Figure 7B:
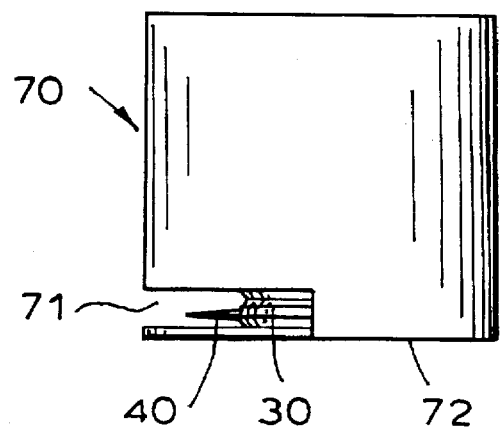
FIG. 7B is a side view of the dispenser shown in FIG. 7.

Turning now to FIGS. 7, 7A and 7B, a dispenser 70 for wheels 30 is shown. The dispenser 70 has generally a cylindrical shape, having a circular top 74 disposed thereupon. There is a semi-circular cut-away 71 in the side of the dispenser 70 sufficient in height to permit a wheel 30 to be dispensed. The dispenser 70 has a generally circular bottom 72 having a cut-out 73 exposing a portion of the wheel 30, and its axle hole 35.

At least one wheel 30 is retained in the dispenser 70 by a frictional force caused a spring 80, which urges the wheel 30 toward the bottom 72. A wheel 30 is dispensed by placing an exposed axle 60 of a device 5 (i.e., when the device 5 is in the open position) into the axle hole 35 of the wheel 30, and aligning the support assembly 15 with the cut-out 73, then, pulling the device handle 10 in a direction away from the dispenser 70 until the wheel 30 is free. The device 5 is now ready to be put in the closed position by pivoting the retaining arm 20 until its axle detent 25 aligns with the axle 60. The device 5 is then ready for use.

The dispenser 70, may be capable of holding a plurality of wheels 30. Where a plurality of wheels 30 are in the dispenser 70, after one wheel 30 is dispensed, the spring 80 urges the remaining wheels 30 toward the bottom 72. Accordingly, another wheel 30 is in position to be dispensed.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. An apparatus for testing nerve pathways through skin sensitivity, comprising:
   a support assembly;
   an axle affixed to the support assembly;
   a wheel having an axle hole adapted to receive the axle, and a plurality of tines extending radially therefrom, each of the tines have a nerve-stimulating portion at a distal end; and
   a retaining assembly for rotatably securing the wheel in position on the axle, the retaining assembly being rotatable relative to the axle to secure the wheel in position and to facilitate removal and replacement of the wheel.

2. The apparatus claimed in claim 1, wherein the retaining assembly is sufficiently movable by hand relative to the axle to permit the removal and replacement of the wheel without the aid of tools.

3. The apparatus claimed in claim 1, wherein the axle hole is in the center of the wheel.

4. The apparatus claimed in claim 1, wherein the wheel has a center and a perimeter, and the thickness of the wheel is greater at the center and smaller at the perimeter.

5. The apparatus claimed in claim 3, wherein the axle hole extends laterally through the wheel.

6. The apparatus claimed in claim 1, wherein the wheel and the tines are made of ABS.

7. The apparatus claimed in claim 1, further comprising a handle connected to the support assembly, wherein the handle and the support assembly are made of ABS.

8. The apparatus claimed in claim 1, wherein the tines have a shape such that the tines are broader than the nerve-stimulating portion at a proximal end.

9. The apparatus claimed in claim 1, wherein the tines are spaced such that the distal ends of the tines are between 3 millimeters and 6 millimeters apart.

10. The apparatus claimed in claim 1, wherein the tines have a shape that is generally conic.

11. The apparatus claimed in claim 1, wherein the tines have a shape that is generally pyramidic.

12. The apparatus claimed in claim 1, wherein the retaining assembly is pivotally mounted to the support assembly.

13. The apparatus claimed in claim 12, wherein the retaining assembly pivots in a plane normal to the axle.

14. The apparatus claimed in claim 1, wherein the retaining assembly is pivotally mounted to the axle, and the retaining assembly can be pivoted from a position perpendicular to the axle to a position parallel to the axle.

15. An apparatus for testing nerve pathways through skin sensitivity, comprising:
   a wheel having a plurality of tines extending radially therefrom, the tines have a nerve-stimulating portion at a distal end, the wheel also having an axle nub protruding laterally therefrom, the axle nub including at least two nub portions and a biasing member located between the at least two nub portions for biasing the at least two nub portions away from each other,
   a support assembly having an integral handle, the support assembly comprising an axle detent; and
   a retaining assembly for rotatably securing the wheel in a position with the axle nub of the wheel aligned with the axle detent of the support assembly and the biasing member forcing the at least two nub portions into engagement with the axle detent.

16. The apparatus claimed in claim 15, wherein the support assembly is movable with respect to the retaining assembly to facilitate insertion and removal of the wheel.

17. The apparatus claimed in claim 15, wherein the axle nub is located at the center of the wheel.

18. The apparatus claimed in claim 15, wherein the wheel and the tines are made of ABS.

19. The apparatus claimed in claim 15, wherein the support assembly and the retaining arm are made of ABS.

20. The apparatus claimed in claim 15, wherein the wheel has a thickness which is greater at the center and smaller at the perimeter.

21. The apparatus claimed in claim 15, wherein the tines have a shape such that the tines are broader than the distal end at the proximal end.

22. The apparatus claimed in claim 15, wherein the tines are spaced such that the distal ends of the tines are between 3 millimeters and 6 millimeters apart.

23. The apparatus claimed in claim 15, wherein the tines have a shape that is generally conic.

24. The apparatus claimed in claim 15, wherein the tines have a shape that is generally pyramidic.

25. The apparatus claimed in claim 15, wherein the axle nub is biased outward from the wheel by a spring.

26. An apparatus for testing nerve pathways through skin sensitivity, comprising:
   a support assembly;
   an axle affixed to the support assembly;
   a wheel having an axle hole adapted to receive the axle, and a plurality of tines extending radially therefrom, each of the tines have a nerve-stimulating portion at a distal end; and
   a retaining assembly for rotatably securing the wheel in position on the axle, the retaining assembly being movable to a position opposite to the axle and the support assembly such that the wheel and the axle are located between the support assembly and the retaining assembly to facilitate removal and replacement of the wheel.

* * * * *